US006184340B1

(12) United States Patent
Smith et al.

(10) Patent No.: US 6,184,340 B1
(45) Date of Patent: Feb. 6, 2001

(54) CHEMICAL DISSOLUTION OF POLY (VINYLALCOHOL) ITEM OR WOVEN OR NON-WOVEN FABRIC WITH ANTIMICROBIAL ACTION

(75) Inventors: Kim R. Smith, Woodbury; Shaun P. Kennedy, North Oaks, both of MN (US)

(73) Assignee: Ecolab Inc., St. Paul, MN (US)

( * ) Notice: Under 35 U.S.C. 154(b), the term of this patent shall be extended for 0 days.

(21) Appl. No.: 09/360,997

(22) Filed: Jul. 26, 1999

(51) Int. Cl.$^7$ ...................................................... C08F 6/00
(52) U.S. Cl. ................................................................ 528/480
(58) Field of Search .............................................. 528/480

(56) References Cited

U.S. PATENT DOCUMENTS

| | | | |
|---|---|---|---|
| 4,073,994 | 2/1978 | Baatz et al. | 428/265 |
| 4,427,409 | 1/1984 | Gregorian et al. | 8/107 |
| 5,181,967 | 1/1993 | Honeycutt | 134/42 |
| 5,196,470 | 3/1993 | Anderson et al. | 524/379 |
| 5,207,837 | 5/1993 | Honeycutt | 134/42 |
| 5,208,104 | 5/1993 | Ueda et al. | 428/364 |
| 5,258,422 | 11/1993 | Chang et al. | 523/124 |
| 5,268,222 | 12/1993 | Honeycutt | 428/224 |
| 5,470,653 | 11/1995 | Honeycutt et al. | 428/357 |
| 5,472,518 | 12/1995 | Patnode et al. | 134/34 |
| 5,486,418 | 1/1996 | Ohmory et al. | 428/397 |
| 5,508,101 | 4/1996 | Patnode et al. | 428/286 |
| 5,567,444 | 10/1996 | Hei et al. | 424/616 |
| 5,567,510 | 10/1996 | Patnode et al. | 428/288 |
| 5,620,786 | 4/1997 | Honeycutt et al. | 442/50 |
| 5,630,972 | 5/1997 | Patnode et al. | 264/103 |
| 5,650,219 | 7/1997 | Honeycutt | 428/229 |
| 5,661,217 | 8/1997 | Honeycutt et al. | 525/62 |
| 5,685,756 | 11/1997 | Noda | 442/327 |
| 5,707,731 | 1/1998 | Honeycutt et al. | 428/357 |
| 5,747,584 | 5/1998 | Noda | 524/801 |
| 5,762,716 | 6/1998 | Lockard et al. | 134/2 |
| 5,823,139 | 10/1998 | Ito | 119/171 |
| 5,840,423 | 11/1998 | Sano et al. | 438/364 |
| 5,849,401 | 12/1998 | El-Afandi et al. | 428/215 |
| 5,858,443 | 1/1999 | Hei et al. | 426/506 |

FOREIGN PATENT DOCUMENTS

7258939 A2   10/1995  (JP) .

*Primary Examiner*—Terressa M. Boykin
(74) *Attorney, Agent, or Firm*—Merchant & Gould P.C.

(57) ABSTRACT

With the advent of disposable items made from or bonded by polyvinylalcohol polymers, particularly highly hydrolyzed polyvinylalcohol of limited water solubility, the disposal of used contaminated items has become a significant problem. These disposable products are typically used once and then discarded. During use, the items often come into contact with infective biological liquids and solids that can contain bacteria, viral particles, fecal matter, blood, mucus, etc. This large volume of disposable and often contaminated materials poses a significant problem to the hospitality and healthcare industries. Previously, such disposables are often sterilized using autoclave (high temperature steam) digestion to render the pathogen content substantially harmless. Such a process is time consuming due to the large volume of disposable materials and can be energy wastefull. We have found that polyvinylalcohol containing fabric materials can be treated with an aqueous alkaline treatment or with an alkaline oxidant for the purpose of rendering the pathogens harmless and dissolving the polyvinylalcohol non-woven for disposal purposes.

26 Claims, No Drawings

CHEMICAL DISSOLUTION OF POLY (VINYLALCOHOL) ITEM OR WOVEN OR NON-WOVEN FABRIC WITH ANTIMICROBIAL ACTION

FIELD OF THE INVENTION

The invention relates to disposal methods and reduction of microbial contamination for a used or contaminated polyvinylalcohol (PVOH) item. An important class of PVOH items are items used in health care and other industries and woven or non-woven fabrics and articles that are contaminated in use and need to be sanitized before disposal. Further, the invention relates to an aqueous treatment that can render a pathogen population in a contaminated item, harmless and can also liquefy and promote the easy convenient disposal of polyvinylalcohol containing items.

BACKGROUND OF THE INVENTION

In the past, hospital and hospitality industries often used conventional cotton and woven fabric materials for a variety of hospital uses. Because of the time involved in collecting, laundering, sanitizing and reusing or recycling conventional fabric materials, replacements for such materials have been sought. One form of replacement including disposable, typically woven or non-woven, fabrics have found substantial use in hospitality and healthcare industries. Such non-woven materials are often made from or bonded with polyvinylalcohol materials. Polyvinylalcohol can be formed into fibers or can be formulated into adhesives which make up structural components of a non-woven fabric material. Non-wovens also can often contain a variety of other ingredients and components to make up fully functional gown, cap, shoe cover, drape, wipe, absorbent article or other component. However, in large part, the polyvinylalcohol materials can act either to maintain the integrity of the unit or can act as the main structural component of the non-woven fabric. Polyvinylalcohol resins have also been used in the manufacture of a variety of items that contain cast, extruded, molded or otherwise manufactured items (apart from woven or non-woven fabrics) that are made of polyvinylalcohol components. Such items can include adhesive materials, films, rigid and non-rigid containers, permeable and non-permeable tubing, permeable and non-permeable membranes, and a variety of other structures. Please note that such structures can contain both fabric and non-fabric components made from polyvinylalcohol resins.

Polyvinylalcohol typically comes in a variety of grades having varieties of water solubility. Partially hydrolyzed polyvinylalcohol, having a hydrolysis degree of about 87 to 88%, is typically an easily solubilized material using cold water. Fully hydrolyzed materials having a degree of hydrolysis of between about 90 and 95% have a reduced cold water solubility as the degree of hydrolyzing increases. Super-hydrolyzed polyvinylalcohol grades typically have a very low cold water solubility and are minimally soluble in aqueous solutions at ambient (room or typical indoor environmental temperature for employees, typically about 20 to 35° C.) temperatures. The water solubility of the polyvinylalcohol polymer can be reduced further by the presence of other typically hydrophobic monomers in the polymer backbone. Such monomers can include ethylene, propylene, vinyl chloride, vinyl alcohol esters, derivatized vinyl alcohol moieties such as those found in polyvinylbutyral, acrylic monomers and others well known to one of ordinary skill in the art. A small proportion of a co-monomer can substantially reduce aqueous solubility.

Non-woven items, woven items, molded sheet or film items made from or formed from polyvinylalcohol fibers or adhesive compositions can be substantially resistant to aqueous materials if the polyvinyl alcohol is selected from the more hydrolyzed or hydrophobic materials. The water solubility of these materials is unique since one would intuitively assume that materials with a high degree of hydrolysis (high proportion of hydroxyls from hydrolysis) would be more water soluble. However, the reverse is true since the reduced acetate content of the polyvinylalcohol results in polymer coiling due to intramolecular hydrogen bonding. These polymer properties result in substantially poorer water solubility as the hydrolysis content increases. Super-hydrolyzed (greater than about 99 wt. % hydrolyzed) polyvinylalcohol is very difficultly solubilized in cold water and when incorporated into a disposable item, can even be more resistant to the action of aqueous solutions because of the protective nature of the this overall structure.

Further, when used in hospitality and healthcare organizations, PVOH items, woven and non-woven materials can often come into contact with pathogenic materials. Non-wovens, in particular, can come into contact and can absorb a variety of biological fluids including whole blood, blood fractions; including red blood cells, white blood cells, platelets, serum, plasma; fecal material, urine, ascites, lymphatic fluids, hair, skin and other natural materials. Similarly, in the hospitality industry such non-woven materials can also come into contact with a more narrow range of biological materials. However, these materials can also be pathogenically hazardous. Because these materials are single use materials and because they are often are biohazards due to substantial pathogenic contamination, the disposal of these materials is a significant problem.

Currently we are aware of two approaches of promoting the disposal of woven and non-woven materials made using polyvinylalcohol. In one approach, the woven or non-woven materials are contacted with very high temperature water to maximize the rate of solubility of the materials, resulting in a disposable solution or dispersion of the components making up the disposable item or items. Our experience in using hot water for the purpose of dissolving and disposing polyvinylalcohol containing non-wovens has shown us that even in very hot water, water at 90° C. to 99° C. and higher, the dissolution rate for the certain polyvinylalcohol items is quite slow for efficient operations. Disposing of highly hydrolyzed polyvinylalcohol (99%+hydrolysis) containing non-woven items simply using very hot water can take in excess of one day, often up to three days for complete dissolution. We believe that any successful disposal method for treating polyvinylalcohol non-wovens will take less than 4 hours, typically less than 2 hours. Further, such hot water treatments often do not render the dissolved polymer free from biohazard pathogens. Examples of highly hydrolyzed polyvinylalcohol absorbent technology designed for hot water dissolution include: Honeycutt, U.S. Pat. Nos. 5,707, 731 and 5,470,653, disclosing a mop head from highly hydrolyzed PVOH and its disposal soluble in hot water; Honeycutt, U.S. Pat. No. 5,650,219, disclosing a process for controlling PVOH solubilization temperature; Honeycutt, U.S. Pat. No. 5,661,217, disclosing manufacture of molded parts from highly hydrolyzed PVOH; Honeycutt, U.S. Pat. Nos. 5,628,222 and 5,207837, disclosing a composite highly hydrolyzed PVOH disposable fabric and its disposal in hot water; Honeycutt, U.S. Pat. No. 5,181,967, disclosing disposal of highly hydrolyzed PVOH utensils in hot water.

A second approach to disposing such materials includes the use of a chemically modified polyvinylalcohol polymer composition. The polymers are specially modified to make the polymers more suitable for alkaline digestion and subsequent dissolution. In our experiences using specially modified polyvinylalcohol polymers that are modified to be sensitive to alkaline dissolution can lead to relatively efficient disposal of non-woven materials. However, the costs of the specially modified polyvinylalcohol can be substantial while the use of the alkali digestion can often not achieve full decontamination and elimination of biohazard. Examples of PVOH items modified for disposal via alkaline dissolution include: Patenode in U.S. Pat. Nos. 5,630972, 5,567,510, 5,472,518, and 5,508,101, all disclosing a dispersible PVOH copolymer composition and a method of making the composition dispersible via alkaline digestion.

A substantial need exists for improved processes for disposing of used or contaminated polyvinylalcohol items, particularly highly hydrolyzed PVOH containing disposable items with simultaneous substantial reduction or elimination of biohazard populations permitting to safe disposal.

BRIEF DISCUSSION OF THE INVENTION

The invention relates to a safe and convenient method of disposing of polyvinylalcohol containing fabricated, woven and non-woven disposable items that can be accomplished while rendering any pathogen contamination substantially harmless for human contact. The method comprises contacting a polyvinylalcohol containing disposable item with an oxidant material in an aqueous solution for sufficient period of time to solubilize a substantial proportion of the polyvinylalcohol while at the same time substantially reducing the population of biohazardous or pathogenic components to a level providing for safe disposal of the item. The product of the process is an effluent comprising a solution or suspension of the PVOH components dissolved in an aqueous medium having a substantially reduced pathogen, microbial population. Such a material can be easily disposed into conventional municipal waste water systems with little biohazard risk. The oxidants used in this invention are well-known as active microbiocidal compositions. In this invention, the oxidants act to kill pathogens or other microbes in or on the polyvinylalcohol material. Further, the nature of the oxidant material is such that the oxidant can, under appropriate conditions, chemically degrade the polyvinylalcohol in a way such that the dissolution of the polyvinylalcohol is made much more rapid than the dissolution rate resulting from simple hot water or alkali digestion. Such a chemical attack is different from the primarily dissolution based mechanism of the prior art which simply relies on the chemical solubility of standard polyvinylalcohol polymers and modified polyvinylalcohol polymers for dissolution purposes. Further, the absence of antimicrobially active chemicals in the prior art dissolution solutions reduces the antimicrobial properties of the prior art systems.

For the purpose of this patent application, the term "pathogen" connotes any virus, single cell or multicellular organism that can be harmful, dangerous or cause illness in humans. Such pathogens include a large variety of bacteria, a large variety of fungi, a large selection of multicellular or parasitic organisms, a number of viral strains and a large variety of materials that can be produced by these organisms including toxins, spores, dormant microorganisms, virus and other monocellular or multicellular structures. Particularly important pathogens are antibiotic resistant bacteria, dangerous viruses including HIV, Hepatitis A and B, and others. Included in such a category are eggs of multicellular parasites and other cells that can grow into harmful multicellular organisms.

The term "polyvinylalcohol item" includes any item using polyvinyl alcohol as a structural component or an adhesive. The polyvinylalcohol can be dissolved in whole or in part using the oxidizing aqueous solutions of the invention. Such items are often manufactured in the form of woven or non-woven articles made from polyvinyl alcohol thread or yarn. Such articles are often woven in conventional weaving methods or formed into non-woven fabrics using conventional non-woven fabric forming technologies. In large part, the woven and non-woven fabrics of the invention are those that can be used in a variety of end uses that can contaminate the fabric and that can either protect or promote the growth of harmful microorganisms. Such contamination can arise in hospitals, restaurants, hotels, slaughterhouses, diaries, food processing facilities, in the household, in nurseries or other places where organic wastes can contaminate a woven or non-woven article. Particularly harmful or dangerous wastes involve materials that are derived from mammals including the human body, pets, agricultural livestock, etc. Such wastes include blood, feces, urine, blood fractions, ascites, bile, lymph fluids, cerebral spinal fluid, etc. Such materials can be the source of a relatively small population of microorganisms or a very large population of microorganisms in the contaminated items. The nature of the contamination and the woven and non-woven fabric can provide a location that can protect or promote the growth of such microorganisms into harmful populations.

For the purpose of this patent application, the term polyvinylalcohol (PVOH) typically refers to a vinyl polymeric material that is at least 15 mole % vinyl alcohol (the theoretical vinyl alcohol monomer is $CH_2=CH—OH$ does not exist, but exists as a $—CH_2—CH(OH)—$ moiety in the polymer). Such materials can contain a substantial proportion of ethylene, propylene or other vinyl monomers further including vinyl, chloride, acrylics, etc. Typically, the polyvinylalcohols of this invention are not polyvinylalcohols modified for alkaline dissolution, but are "conventional" polyvinylalcohols. The preferred polyvinylalcohol of the invention is a partially hydrolyzed (85 and 92 wt % hydrolysis) or fully hydrolyzed material (up to 98.5% hydrolysis) or super hydrolyzed polyvinylalcohol having a degree of hydrolysis between 98 and 100 wt %.

DETAILED DISCUSSION OF THE INVENTION

The process of the invention involves contacting a polyvinylalcohol item with an aqueous solution comprising an oxidant at an acidic, neutral or alkaline pH to dissolve the polyvinylalcohol item and kill or render harmless any microorganism present on the used or contaminated polyvinylalcohol item. The pH is selected that is appropriate for the oxidizing agent used. For example, peracid materials are often used at an acid pH while chlorine materials are often used at an alkaline pH. Lastly, ozone oxidants are often used at mildly acid neutral or alkaline pH. The pH selected for each oxidant material is well understood by one of ordinary skill in the art. More commonly, the method uses an aqueous oxidant to dissolve a polyvinylalcohol manufactured, woven or non-woven used article and render adsorbed biohazards innocuous. Such articles often can contain a contaminating substance that can be a source of or a place for growing populations of harmful pathogens.

The process of the invention can use virtually any oxidizing system that can both dissolve or degrade polyvinylalcohol materials to the degree that the polyvinylalcohol is fully solubilized in a relatively short period of time, typically less than about 6 hours, preferably less than about 3 hours. The oxidant used is commonly an oxidant that can cleave the polyvinylalcohol materials at or near a hydroxyl group. Such polymer cleavage reaction typically reduces the molecular weight of the polyvinylalcohol polymer, thus speeding dissolution. The oxidant is also used at a concentration and temperature such that the resident biohazards in the polyvinylalcohol item are rendered innocuous for human contact. Any oxidant that can meet these criteria can be used in the invention.

Preferred oxidants for use in the invention include chlorine-based oxidants such as chlorine gas, hypochlorite compounds, N-chloro compounds and chlorine dioxide compounds. A further class of useful oxidant materials include peroxygen-containing materials such as hydrogen peroxide or the percarboxylic acid compounds typically made by reacting a mono- or dicarboxylic acid with a source of active oxygen such as hydrogen peroxide to form an equilibrium mixture of peracid hydrogen peroxide and carboxylic acid in active solution. Lastly, a useful oxidant comprises ozone in aqueous solution. Such aqueous solutions are typically prepared with a concentration of ozone that is sufficient to react with and solubilize the polyvinylalcohol and render the pathogenic population innocuous while consuming the active ozone concentration.

Chlorine-containing oxidizing agents are cost effective disinfectants and polyvinylalcohol-dissolving agents. Chlorine-containing agents are often divided into four general classes including chlorine ($Cl_2$), hypochlorites ($ClO^{-1}$), N-chloro compounds and chlorine dioxide materials. The first three classes are called available chlorine compounds and are related to chlorine by equilibria reactions involving chlorine hypochlorite in a variety of gaseous or solution forms. The total concentration amount of chlorine based oxidants is often expressed as available chlorine or less frequently as active chlorine. Active available chlorine is the equivalent concentration or amount of chlorine ($Cl_2$) gas needed to make the equivalent oxidant. Active chlorine is that equivalent concentration or amount of chlorine atoms that can accept two electrons. This is a concentration; not a description of the reaction mechanism of the oxidant. Because chlorine gas only accepts two electrons as does HOCl and monochloroamines, it has only one active chlorine atom according to the definition. Thus, the active chlorine always is one-half of the available chlorine. The available chlorine is usually mentioned by iodometric titration using known techniques. Another way of measuring available chlorine uses the following equation:

weight of available chlorine=70.9×moles of oxidant×number of active chlorine atoms per molecule.

In solution, the concentration of available chlorine is in the form of hypochlorite, hypochlorous acid is called "free-available" chlorine. Commercially important solid available chlorine bleaches are usually more stable than concentrated aqueous hypochlorite solutions. Solid available chlorine decomposes very slowly in sealed containers, particularly if kept dry and away from heat. Most solid chlorine sources decompose quickly if exposed to humidity or heat The common forms of such chlorine based oxygens include chlorine gas, sodium hypochlorite, calcium hypochlorite, lithium hypochlorite, chlorinated sodium tripolyphosphate and hypochlorous acid, sodium dichloroisocyanurate dihydrate, halogenated hydantoins, sodium N-chlorobenzene sulfonamide (Chlorimene B), sodium and fluoro p-toluene sulfonamine (Chlorimene T) and other similar chlorinated organic sources. These available chlorine sources are commonly made available in a variety of useful formats including concentrated aqueous solutions and containers of the solid chlorine yielding compounds. The active chlorine-containing materials would be used at a concentration of about 0.01 to 20 weight percent of active chlorine in aqueous solution for PVOH dissolution and concurrent microbial decontamination, preferably 0.1 to 10 weight percent of active chlorine in the aqueous solution. The concentration of the active ingredients in the treatment composition can be adjusted using make-up amounts of the concentrate material delivered during treatment. The concentration of active chlorine may be increased or decreased while still remaining within the scope of the invention.

The process of the invention can use a combination of peracid, hydrogen peroxide and mono-, di- or polycarboxylic acid. The compositions of the invention contain water, peracid acid, hydrogen peroxide and unoxidized acid across a relatively broad range of concentrations. Peracetic acid and mixtures of peracetic acid with other monocarboxylic and dicarboxylic acids are preferred. Peracetic acid is a freely water soluble liquid having a pungent, acrid odor resembling acetic acid, but with a strong oxidizing character. The antimicrobial compositions of the invention also comprise a proportion of hydrogen peroxide. The peracid, carboxylic acid, hydrogen peroxide mixtures would be used at a concentration of about 0.01 to 20 weight percent peracid in aqueous solution for PVOH dissolution and concurrent microbial decontamination, preferably 0.1 to 10 weight percent of peracid in the aqueous solution. These concentrations of peracid, carboxylic acid, and hydrogen peroxide may be increased or decreased while still remaining within the scope of the invention. The concentration of the active ingredients in the treatment composition can be adjusted using make-up amounts of the concentrate material delivered during treatment.

The invention comprises a carboxylic acid oxidizable to a peracid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three or more carboxyl groups. Carboxylic acids have a tendency to acidify aqueous compositions in which they are present as the hydrogen atom of the carboxyl group is active and may appear as an anion.

The carboxylic acid constituent within the present composition when combined with aqueous hydrogen peroxide generally functions as an antimicrobial agent as a result of the presence of the active hydrogen atom. Moreover, the carboxylic acid constituent within the invention maintains the composition at an acidic pH. Carboxylic acids which are generally useful in the process of the invention are those which comprise percarboxylic acids. Percarboxylic acid generally have the formula $R(CO_3H)_n$, where R is an alkyl, arylalkyl, cycloalkyl, aromatic or heterocyclic group, and n is one, two, or three and named by prefixing the parent acid with peroxy. While peroxy carboxylic acids are not as stable as the unoxidized material, their stability generally increases with increasing molecular weight. Thermal decomposition of these acids may generally proceed by free radical and non-radical paths, by photodecomposition or radical-induced decomposition or by the action of metal ions or complexes. Percarboxylic acids may be made by the direct acid catalyzed equilibrium action of 30–98 wt % hydrogen peroxide with the carboxylic acid, by autoxidation of aldehydes, or from acid chlorides and hydrides, or carboxylic anhydrides with hydrogen or sodium peroxide.

Percarboxylic acids useful in this invention include peracetic acid, perpropionic acid, perbutyric acid, peroctanoic acid, perglycolic acid, perglutaric acid, persuccinic acid, perlactic acid, percitric acid, perdecanoic acid or mixtures thereof. These percarboxylic acids have been found to provide good antimicrobial action with good stability in aqueous streams. In addition to peracetic, peroctanoic and perdecanoic, particularly preferred percarboxylic acids include perpropionic, perbutyric, perglycolic, perlactic and percitric acids.

The process of the invention can use a combination of peracetic acid with other percarboxylic acids, preferably, those named above and particularly, peroctanoic acid. This combination of percarboxylic acids has been found to provide preferred antimicrobial efficacy and stability in the presence of high organic loads. Generally, within the sanitizer concentrate, the concentration of, for example, peroctanoic acid may range from about 10 wt-% to 90 wt-% and preferably from about 10 wt-% to 20 wt-%. The concentration of peracetic acid may range from about 10 wt-% to 90 wt-% and preferably from about 80 wt-% to 90 wt-%.

Peracetic acid is the preferred peracid. Peracetic acid is a peroxy carboxylic acid having the formula:

$CH_3COOOH$.

Generally, peracetic acid is a liquid having an acrid odor at higher concentrations and is freely soluble in water, alcohol, ether, and sulfuric acid. Peracetic acid may be prepared through any number of means known to those of skill in the art including preparation from acetaldehyde and oxygen in the presence of cobalt acetate. A 50% solution of peracetic acid may be obtained by combining acetic anhydride, hydrogen peroxide and sulfuric acid. Other methods of formulation of peracetic acid include those disclosed in U.S. Pat. No. 2,833,813, which is incorporated herein by reference.

The antimicrobial composition of the invention may also comprise a hydrogen peroxide constituent with or in the absence of oxidizable acids or the peracids themselves. Hydrogen peroxide in combination with the percarboxylic acid provides a surprising level of antimicrobial action against microorganisms despite the presence of high loadings of organic sediment.

While many oxidizing agents may be used, hydrogen peroxide is generally preferred for a number of reasons. After application of the $H_2O_2$ germicidal agent, the residue left can decompose to water. Deposition of decomposition products on the surfaces such as a washing machine would therefore be minimized.

Hydrogen peroxide ($H_2O_2$) has a molecular weight of 34.014 and it is a weakly acidic, clear, colorless liquid. The four atoms are covalently bonded in a non-polar H—O—O—H structure. Generally, hydrogen peroxide has a melting point of –0.41° C., a boiling point of 150.2° C., a density at 25° C. of 1.4425 grams per $cm^3$ and a viscosity of 1.245 centipoise at 20° C. Generally, the concentration of hydrogen peroxide within the concentrate composition used in the process of the invention ranges from about 1 weight percent to about 80 weight percent, preferably from about 3 weight percent to about 50 weight percent, and most preferably from about 5 weight percent to about 35 weight percent. Hydrogen peroxide would be used at a concentration of about 0.01 to 20 weight percent peracid in aqueous solution for PVOH dissolution and concurrent microbial decontamination, preferably 0.1 to 10 weight percent of hydrogen peroxide in the aqueous solution. The concentration of the active ingredients in the treatment composition can be adjusted using make-up amounts of the concentrate material delivered during treatment. These concentrations of hydrogen peroxide may be increased or decreased while still remaining within the scope of the invention.

In the process of the invention the aqueous solution containing ozone ($O_3$) is contacted with the PVOH item. The basic requirements of the system is that the aqueous solution is contacted with a used or contaminated item. The aqueous solution with ozone results in both dissolution and the substantial kill of microorganisms and the reduction of ozone concentration in the treatment zone. The amount of ozone added to the treatment zone can be easily calculated from the fabric and the challenge soil load concentration. However, proportions of challenge soil load and preferred concentration of ozone is discussed below.

Ozone cannot be easily stored or shipped. Ozone is typically generated on site and is dissolved into aqueous media at a use locus just prior to use. The half life of ozone in neutral solutions is about 3–10 minutes and less as pH increases. Weak concentrations of ozone may be generated using ultraviolet radiation. Typical production of ozone is made using electrical corona discharge. The process involves obtaining a source of oxygen in a pure form of $O_2$ generally atmospheric oxygen (or enriched air) containing greater than about 21 volume % oxygen. The source of oxygen is passed between electrodes across which a high voltage alternating potential is maintained. The potential is established across the electrodes which are configured to prevent arching. As oxygen molecules enter the area of potential, a corona is created having a proportion of free atomic oxygen dissociated from an oxygen molecule ($O_2$). The high energy atomic ion (O) when combined with oxygen ($O_2$) form a mixture of oxygen and ozone ($O_3$). These generators are available commercially. The ozone containing aqueous mixture is generally contacted with an aqueous solution through bubbling or other gas dispersion techniques to introduce an antimicrobial concentration of ozone into the aqueous medium. The contact between ozone and the aqueous medium is then engineered to maximize the absorption of ozone when compared to the rate of decomposition of ozone in the alkaline aqueous medium and the required ozone concentration in the water.

The activity of ozone in the aqueous medium of the invention can be improved by introducing ozone into the smallest possible diameter bubble formation. Small bubbles promote the dissolution of ozone into the bulk aqueous solution. Additionally, surface active agents which lower the gas liquid interfacial tension can be used to enhance ozone gas transport to the aqueous medium. Rapid dissolution of ozone can reduce the tendency to off gas into the atmosphere, and cause reactions with solution components to produce oxidized species and promote the effective use of ozone. Ozonized solutions can contain ozone in increasing proportions as temperatures decrease. 60° C. aqueous solutions are rapidly depleted of ozone by off gassing. In sharp contrast, aqueous media at 0° C. can contain a fairly constant proportion of ozone at about 35 ppm.

The stability of ozone in aqueous solutions decreases as alkalinity increases. The half life of ozone in 1 N sodium hydroxide is less than 10 seconds. For the purpose of the invention involving concentrations of ozone in aqueous solution, the term "total ozone" relates to the amount of ozone added to the aqueous phase from the gas phase. typically these total ozone levels in the gas phase range from about 1 to about 1000 parts of ozone to one million parts of total aqueous phase. Measured ozone is the apparent concentration of ozone (as $O_3$) in aqueous solution. The difference between total ozone and measured ozone relates to the amount of ozone that apparently becomes stored in aqueous solution by reaction with organic and inorganic species to form ozonized or oxidized materials which can be a source of oxidizing potential.

The aqueous oxidant antimicrobial composition of the invention may also comprise any number of adjuvants. Specifically, the composition of the invention may comprise stabilizing agents, wetting agents, as well as pigments or dyes among any number of constituents which may be added to the composition. Stabilizing agents may be added to the composition of the invention to stabilize the peracid and hydrogen peroxide and prevent the premature oxidation of this constituent within the composition of the invention. Chelating agents or sequestrants generally useful if stabilizing agents in the invention include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethylden-1, 1-diphosphonic acid $(CH_3C(PO_3H_2)_2 OH)$, amino [tri(methylene phosphonic acid)]$([CH_2PO_3H_2]_2$ (ethylene diamine [tetra methylene-phosphonic acid)], 2-phosphene butane-1,2,4-tricarboxylic acid, as well as the alkyl metal salts, ammonium salts, or alkanol amine salts, such as mono-, di- or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Also useful in the composition of the invention are wetting and defoaming agents. Wetting agents function to increase the penetration activity of the antimicrobial composition of the invention. Wetting agents which may be used in the composition of the invention include any of those constituents known within the art to raise the surface activity of the composition of the invention.

Along these lines surfactants, and especially nonionic surfactants, may also be useful in the present invention. Nonionic surfactants which may be useful in the present invention are those which comprise ethylene oxide moieties, propylene oxide moieties, as well as mixtures thereof, and ethylene oxide-propylene oxide moieties in either heteric or block formation. Additionally useful in the present invention are nonionic surfactants which comprise alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to an alkyl chain where the ethylene oxide and propylene oxide moieties may be in any randomized or ordered pattern and of any specific length. Nonionic surfactants useful in the present invention may also comprise randomized sections of block and heteric ethylene oxide propylene oxide or ethylene oxide-propylene oxide.

Generally, the concentration of nonionic surfactant, if used, in the invention may range from about 0.1 wt-% to about 50 wt-% of the concentrate composition, preferably from about 0.1 wt-% to about 20 wt-% of the concentrate composition, and most preferably from about 0.1 wt-% to about 10 wt-% of the concentrate composition. The composition used in the process of the invention may also contain additional ingredients as necessary to assist in defoaming. Generally, defoamers which may be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof. To this end, one of the more effective antifoaming agents comprises silicones. Silicones such as dimethyl silicone, glycol polysiloxane, methylphenol polysiloxane, trialkyl or tetralkyl silanes, hydrophobic silica defoamers and mixtures thereof may all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200™ from Dow Corning Corporation which are both food grade type silicones among others. These defoamers are generally present at a concentration range from about 0 wt-% to 5 wt-%, preferably from about 0 wt-% to 2 wt-%, and most preferably from about 0 wt-% to about 1 wt-%.

The invention may also contain any number of other constituents as necessitated by the application, which are known to those of skill in the art and which may facilitate the activity of the present invention.

The composition used in the invention may comprise:

|  | Useful | Working | Preferred |
|---|---|---|---|
|  | Concentrate Composition (Wt-%) | | |
| Oxidant | 0.1–80 | 3–50 | 5–35 |
| Sequestrant | 0–10 | 0.1–5 | 0.1–4 |
| Water | Balance | Balance | Balance |
|  | Initial Concentration in Aqueous Treatment Use Solution (Wt %) | | |
| Constituent |  |  |  |
| Oxidant | 0.01–20 | 0.1–10 | 0.1–5 |
| Sequestrant | 0–2.5 | 0.1–0.7 | 0.1–0.5 |

Once the aqueous oxidant antimicrobial of the invention is applied to any given aqueous system for PVOH dissolution, the antimicrobial will be subjected to a demand resulting from microbes present in the system as well as other organic or inorganic material present including the PVOH item itself. As a general guideline, not limiting of the invention, the following concentrations of antimicrobial may be found after demand. The actual residual amount depends on challenge load and oxidant concentration.

|  | Preferred Residual Concentration (Wt %) After Dissolution and Organic Demand | | |
|---|---|---|---|
|  | Useful | Working | Preferred |
| Oxidant | 0–20 | 0.1–5 | 0.1–1 |
| Sequestrant | 0–2.5 | 0.1–0.7 | 0.1–0.5 |

The treatment compositions of the invention can comprise concentrate materials that fall within the following generic formula:

| Treatment Concentrate | | | |
|---|---|---|---|
| Ingredient | Useful Wt % | Working Wt % | Preferred W % |
| Peracetic Acid | 0.1–50 | 0.5–40 | 4–40 |
| Hydrogen Peroxide | 1–50 | 3–40 | 5–30 |
| Acetic Acid | 0.5–90 | 0–60 | 5–50 |
| Sequestrant | 0.1–10 | 0.1–5 | 0.5–2 |
| Water | Balance | Balance | Balance |

The above compositions comprise concentrate materials that can be metered into the PVOH item treatment loci or to an aqueous stream flowing into the loci. As a general guideline, the following table sets forth working ranges of active ingredients in the treatment composition after dilution in the aqueous stream.

| Residual Concentration After Dissolution and Organic Demand | | | |
|---|---|---|---|
| Treatment Constituent | Usefull (Wt %) | Working (Wt %) | Preferred (Wt %) |
| Peracetic Acid | 0–20 | 0–10 | 0–5 |
| Hydrogen Peroxide | 0–20 | 0–10 | 0–5 |
| Acetic Acid | 0–36 | 0–18 | 0–9 |
| Sequestrant |  | 0.01–25 |  |
| Water | Balance | Balance | Balance |

These concentrations are determined using the following formulas:

$$\text{Dosed Concentration} = \frac{\text{grams of active ingredient added}}{\text{grams of liquid solution}}$$

$$\text{Residual Concentration} = \frac{\text{grams of active ingredient detected by analysis after reaction}}{\text{grams of liquid solution}}$$

The compositions of the invention can be used in both batch and continuous processing of polyvinylalcohol items. In batch processing, a heated or unheated vessel can be used to contain the polyvinylalcohol items, water and a sufficient quantity of the oxidant to completely solubilize the polyvinylalcohol into reduced biohazard populations. In batch processing, the vessel is typically charged with the polyvinylalcohol material and water and the oxidant and agitated for a sufficient period of time to dissolve the polyvinylalcohol items. The batch vessel can be exposed to conditions of heat, agitation, increased atmospheric pressure or any other condition that is known to accelerate the dissolution process or improve the degree of biohazard reduction. Obviously, the vessel can be heated to a temperature of up to 100° C. for the aqueous solution or higher if a pressure vessel is used. These reactions and dissolutions can be carried-out in common autoclave installations or washing machines.

The processes of the invention can also be conducted in a continuous or semi-continuous reaction method. In such a continuous reaction method, the process can be conducted by charging a vessel with a quantity of the polyvinylalcohol item and water and into the vessel is charged a continuous stream of the oxidant material. The oxidant material, aqueous or non-aqueous, flows through the vessel continuously dissolving the polyvinylalcohol and continuously removing the dissolved material from the vessel. The vessel contents can be monitored to maximize the dissolution rate and biohazard reduction of polyvinylalcohol items added to the vessel. The polyvinylalcohol item can be charged directly to the vessel or to the stream of oxidant entering the vessel or through any other convenient addition method. One method involves adding the polyvinylalcohol item to an aqueous solution of the oxidant or other aqueous solution, prior to charging the vessel with the polyvinylalcohol item.

During continuous operations in PVOH dissolution and reducing microbial population, a continuous stream of the treatment composition is directed to the use loci. The treatment composition flows into the use loci while an amount of the concentrate must be either continually or intermittently added to the continuous stream to maintain the desired level of oxidant, preferably 1–20 weight percent and more preferably 1–10 weight percent during operations. Exemplary formulas (equilibrium mixtures) of oxidant concentrates are shown below.

EXAMPLE 1

| Ingredient | Wt % |
|---|---|
| Hydrogen Peroxide | 11.1 |
| Sequestrant | 25.3 |
| Water | 41.0 |
| Peracetic Acid | 32.2 |

EXAMPLE 2

| Ingredient | Wt % |
|---|---|
| Hydrogen Peroxide | 27.8 |
| Sequestrant | 1.0 |
| Water | 71.6 |

EXAMPLE 3

| Ingredient | Wt % |
|---|---|
| NaOCl | 15.0 |
| Sequestrant | 1.0 |
| Water | 74.0 |

EXAMPLE 4

| Ingredient | Wt % |
|---|---|
| Ozone | 10–10,000 (ppm) |
| Sequestrant | 1.0 |
| Water | Bal |

EXAMPLE 5

| Ingredient | Wt % |
|---|---|
| Acetic Acid | 6.5 |
| Hydrogen Peroxide | 26.6 |
| Sequestrant | 1.0 |
| Peracetic Acid | 4.7 |
| Water | 61.6 |

Comparative Example A

Dissolution at Neutral pH without Oxidant

A 5 g portion of 1"×3" PVA fabric swatches soluble only in very hot water (U.S. Pat. No. 5,207,837) was placed in 250 mL water and heated to about 190° F. The pH of the system was 7.1. Samples were pulled periodically and examined for reduced size as an indicator of the rate of dissolution.

| Time | Swatch Size |
|---|---|
| 0 | 1" × 3" |
| 0.5 hour | 1" × 3" |
| 1 hour | ½" × ½" |
| 4 hours | ½" × ½" |

Hot water is a poor dissolving agent even if it acts to kill pathogen populations after one hour at elevated temperature. The above results demonstrate the slow dissolution rate of highly crystalline (98% hydrolyzed) PVOH in very hot water. This performance is generally unacceptable for typical institutional or industrial use.

Comparative Example B

Dissolution at Alkaline pH without Oxidant

A 5 g portion of 1"×3" PVA fabric swatches soluble only in very hot water (U.S. Pat. No. 5,207,837 was placed in 250 mL water at pH=11.7 and heated to about 90° C.

| Time | Swatch Size |
|---|---|
| 0 | 1" × 3" |
| 0.5 hour | ½" × 1" |
| 1 hour | ½" × ½" |
| 4 hours | ½" × ½" |

The above results show that use of hot alkaline solutions was not substantially better than hot water for dissolution of PVOH materials.

EXAMPLE 1

Dissolution at Alkaline pH in Presence of Hydrogen Peroxide as Oxidant

A 5 g portion of 1"×3" PVA fabric swatches soluble only in very hot water (see U.S. Pat. No. 5,207,837) was placed in 250 mL 0.3% hydrogen peroxide at pH=10.1 and heated to about 190° F. Samples were pulled periodically and examined for reduced size as an indicator of the rate of dissolution.

| Time | Swatch Size |
|---|---|
| 0 | 1" × 3" |
| 0.5 hour | <1/16" × <1/8" |
| 1 hour | fully dissolved |

The use of the hydrogen peroxide oxidant rapidly reduced the PVOH non-woven to solution in about 1 hour and reduced microbial populations. This result is an acceptable rate for most applications in institutional and industrial operations.

EXAMPLE 2

Dissolution at Neutral pH in Presence of Hydrogen Peroxide as Oxidant

A 5 g portion of 1"×3" PVA fabric swatches soluble only in very hot water (U.S. Pat. No. 5,207,837) was placed in 250 mL 0.3% hydrogen peroxide at pH=7.1 and heated to about 190° F. Samples were pulled periodically and examined for reduced size as an indicator of the rate of dissolution.

| Time | Swatch Size |
|---|---|
| 0 | 1" × 3" |
| 0.5 hour | <1/16" × <1/8" |
| 1 hour | fully dissolved |

Similar results to Example 1 were found even at about neutral pH.

EXAMPLE 3

Dissolution at Alkaline pH in Presence of Sodium Hypochlorite as Oxidant

A 5 g portion of 1"×3" PVA fabric swatches soluble only in very hot water (U.S. Pat. No. 5,207,837) was placed in 250 mL 2% sodium hypochlorite at pH=13 and heated to about 120° F. Samples were pulled periodically and examined for reduced size as an indicator of the rate of dissolution.

| Time | Swatch Size |
|---|---|
| 0 | 1" × 3" |
| 0.5 hour | <1/16" × <1/8" |
| 1 hour | fully dissolved |

Even with reduced temperature (120° F. vs 190° F.), the hypochlorite was very effective in dissolution of the non-woven in less than 1 hour.

We have found that the concentration of oxidant sufficient to dissolve even the highly hydrolyzed polyvinylalcohol articles, about 0.01–20 weight percent, is more than sufficient to also act as an effective antimicrobial. For example, Block in "Disinfection, Sterilization, and Preservation" summarizes hydrogen peroxide as being effective against bacteria at only 1000 ppm and effective against virii at 3 weight percent. Block also reports peracetic acid to be effective against a wide range of microorganisms at less than 2000 ppm and ozone to be both effective at less than 100 ppm.

The above description, examples and data show the effectiveness of using aqueous oxidant materials at extremes of pH and temperature to dissolve highly hydrolyzed polyvinylalcohol items and simultaneously reduce any biohazard pathogenic populations to safe levels. The specification is meant to illustrate the invention and should not be used to limit the claims. Since the invention can be applied to polyvinylalcohol disposal and sanitization processes using a variety of embodiments that do not depart from the spirit and scope of the invention, the invention resides in the claims hereinafter appended.

We claim:

1. A method of disposing of a polyvinylalcohol-containing item, the method comprising:
    (a) contacting the item in an aqueous oxidant solution for a time sufficient to substantially solubilize the polyvinylalcohol in the item creating a solution or dispersion in an aqueous medium of the item constituents; and
    (b) disposing of the aqueous solution or dispersion.

2. The method of claim 1 wherein the time sufficient comprises less than 240 minutes.

3. The method of claim 1 wherein the time sufficient comprises less than 120 minutes.

4. The method of claim 1 wherein the temperature is ambient or higher.

5. The method of claim 1 wherein the treatment is conducted in a washing machine.

6. The method of claim 1 wherein a surfactant is used to reduce the surface tension of the treatment solution.

7. The method of claim 1 wherein the oxidant is an active chlorine compound.

8. The method of claim 1 wherein the oxidant is hypochlorous acid or its salts.

9. The method of claim 1 wherein the oxidant is an inorganic peroxide.

10. The method of claim 1 wherein the oxidant is hydrogen peroxide.

11. The method of claim 1 wherein the oxidant is an organic peroxide.

12. The method of claim 1 wherein the oxidant is a peracid.

13. The method of claim 1 wherein the oxidant is ozone.

14. The method of claim 1 wherein any bacterial, viral, protozoan, spore or otherwise microbial population of the treated PVOH-containing item is reduced in population by the oxidant treatment.

15. The method of claim 14 wherein any bacterial population experiences a at least a 1 log reduction in the population numbers.

16. The method of claim 14 wherein any population of viral particles are substantially rendered harmless by the oxidant treatment.

17. The method of claim 1 wherein the polyvinylalcohol is at least 50% hydrolyzed.

18. The method of claim 1 wherein the polyvinylalcohol is a highly hydrolyzed polyvinylalcohol having a degree of hydrolysis of at least 90 wt %.

19. The method of claim 1 wherein the polyvinylalcohol has a crystallinity of at least 50%.

20. The method of claim 1 wherein the polyvinylalcohol has a crystallinity of at least 90%.

21. The method of claim 1 wherein the polyvinylalcohol-containing item is a woven or nonwoven fabric.

22. The method of claim 1 wherein the polyvinylalcohol-containing item is a mop head.

23. The method of claim 1 wherein the polyvinylalcohol-containing item is a fabric for medical use.

24. The method of claim 1 wherein the polyvinylalcohol-containing item is a fabricated item having a hard surface.

25. The method of claim 1 wherein the polyvinylalcohol-containing item is a container or other packaging material.

26. The method of claim 1 wherein the polyvinylalcohol-containing item dissolves or disperses to release a chemical substance.

* * * * *